United States Patent [19]

Olsen

[11] 4,196,167
[45] Apr. 1, 1980

[54] DRUG DETECTION DEVICE

[75] Inventor: C. Eric Olsen, Ventura, Calif.

[73] Assignee: California Medical Developments, Inc., Ventura, Calif.

[21] Appl. No.: 972,681

[22] Filed: Dec. 26, 1978

[51] Int. Cl.² .................... G01N 33/16; G01N 21/06
[52] U.S. Cl. .................................... 422/61; 128/759; 422/102
[58] Field of Search ............... 23/230 B; 422/99, 102, 422/61; 128/759; 195/127

[56] References Cited

U.S. PATENT DOCUMENTS

| | | | |
|---|---|---|---|
| 3,579,303 | 5/1971 | Pickering | 422/102 |
| 3,715,189 | 2/1973 | Nighohossian et al. | 422/61 |
| 3,768,979 | 10/1973 | Mead et al. | 422/61 |
| 3,876,503 | 4/1975 | Mennen | 195/127 |
| 3,913,564 | 10/1975 | Freshley | 195/127 |
| 3,939,044 | 2/1976 | Wilkins et al. | 195/127 |
| 4,014,748 | 3/1977 | Spinner et al. | 128/759 |

Primary Examiner—R. E. Serwin
Attorney, Agent, or Firm—Jack C. Munro

[57] ABSTRACT

The drug detection device which is composed of a pair of members interconnected together to form an internal enclosed chamber. An elongated swab having an absorbent tip is located within the internal enclosed chamber. One of the members of the housing has attached a pair of separate compartments which are interconnected by a frangible seal and further being interconnected to the internal chamber by a frangible seal. Within each of these compartments there is to be located a different substance and upon breaking of the frangible seal between the compartments, the substances within these compartments are to be intermixed. Upon the breaking of the frangible seal to the internal chamber, the tip of the swab will then become in contact with the intermixed substances. The other member of the housing has attached at its closed end a third compartment and within this third compartment is to be located a third substance. After the tip of the swab has been placed in contact with the drug contact area and caused to come in contact with the first two substances, the tip of the swab is then placed adjacent the third compartment and upon breaking of its frangible seal, the tip of the swab will then be contacted by the third substance. If the tip of the swab was placed in contact with a certain family of drugs, the tip of the swab will then change color. Prior to use of the device of this invention, the pair of members of the device are sealingly closed so as to maintain the device in an uncontaminated condition prior to use.

4 Claims, 5 Drawing Figures

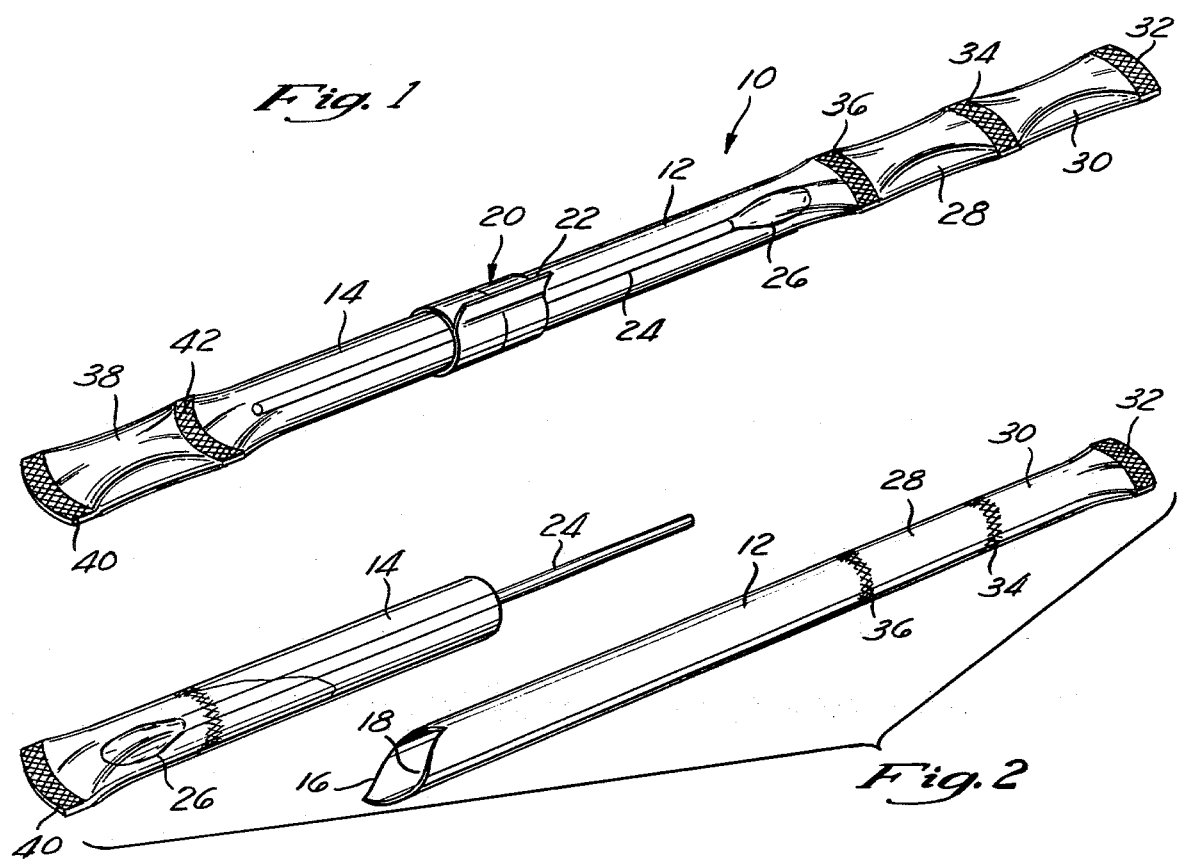
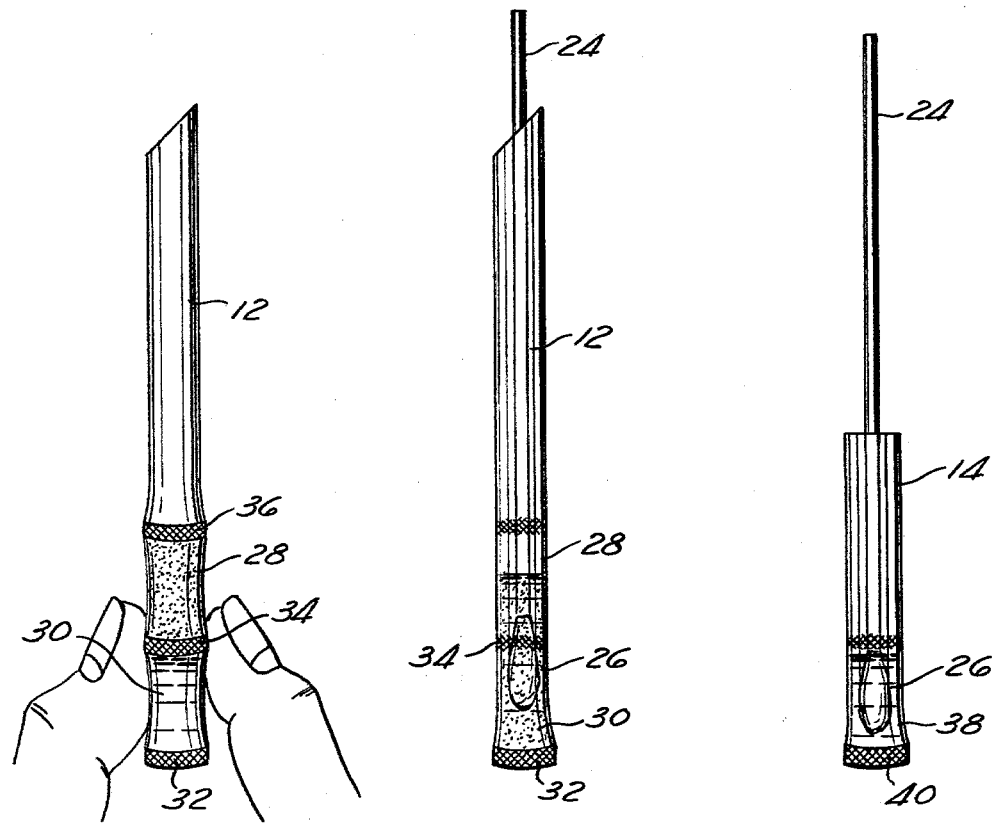

DRUG DETECTION DEVICE

BACKGROUND OF THE INVENTION

The field of this invention relates to testing devices and more particularly to a device which can be used to ascertain the presence of a certain type of drug such as cannabis.

Testing devices of different sorts have been known for a substantial number of years. Within the present day society, there is commonly used a drug which is generally referred to as marijuana. Marijuana as well as the products from marijuana each contain cannabis. Recently there has been discovered a process for ascertaining the presence of cannabis. If a swab having an absorbent tip is placed in contact with a residue of marijuana and that swab was subjected to a certain chemical treatment procedure, then the tip of the swab will alter color indicating the presence of cannabis.

Such a testing procedure is most valuable since prior to this procedure the only known way to determine if a suspect was illegally using marijuana was if a quantity of marijuana was on the suspect's person. However, now if a swab is brought into contact with the suspect's mouth, nose, hands or other parts of his body thought to have come in contact with marijuana, and that swab was tested properly, then the presence of marijuana could be ascertained.

The testing procedure involves the use of three different substances and intermixing of these substances in a certain progression. If they are not used in the proper manner, the test is ineffective. The normal place for a suspect to be caught would normally be in a place other than the confines of a police station or hospital where the testing procedure can be completed in its correct separate steps.

However, there is a need for a testing device which can be readily carried by law enforcement officers and other individuals which can be quickly and easily used in the field to ascertain whether or not a certain suspect has come into contact with marijuana.

SUMMARY OF THE INVENTION

The structure of this invention is summarily described in the Abstract of the Disclosure and refenence is to be had thereto.

The primary objective of this invention is to construct a device which facilitates the detection of any drug which contains cannabis with this drug normally being performed upon the body of a certain individual.

It is a further objective of this invention to construct a device which facilitates testing of an individual in practically any locale not requiring the transporting of that individual to a specific locale.

A still further objective of this invention is to construct a testing device which can be quickly and easily used and which simplifies the testing procedure.

A still further objective of this invention is to construct a testing device which can be manufactured at extremely low cost and therefore facilitating its widespread use.

BRIEF DESCRIPTION OF THE DRAWING

FIG. 1 is an isometric view of the testing device of this invention showing the two separate members of the housing interconnected together in a sealed condition;

FIG. 2 is an isometric view showing the two members of the housing of the device of this invention being separated and with the swab having been removed from its previous location shown within FIG. 1 and inserted into the other member of the housng;

FIG. 3 is a diagramatic view showing the breaking of the frangible seal interconnecting the two compartments attached to the first member of the housing;

FIG. 4 is a view similar to FIG. 3 but showing the tip of the swab in contact with the intermixed substances of the two compartments; and FIG. 5 is an elevational view showing the tip of the swab located within the other of the members of the housing and in contact with a material located within the compartment of this member.

DETAILED DESCRIPTION OF THE SHOWN EMBODIMENT

Referring particularly to the drawing there is shown within FIG. 1 the drug detection device 10 of this invention which is composed primarily of a first member 12 and a second member 14. The first member 12 and the second member 14 are normally to be telescopingly interconnected together with a sliding of the first member 12 within the second member 14 being facilitated by incline section 16 which is formed on the open end of the member 12. The members 12 and 14, when interconnected together, form an enlarged internal chamber 18. A housing formed of the members 12 and 14 is to be constructed of a transparent material such as a clear plastic.

The members 12 and 14 when interconnected together as shown in FIG. 1 are to be normally sealed to protect the internal chamber 18 from contamination by foreign substances by a sealing means 20. The sealing means 20 merely comprises a overlying tape, usually of plastic, which can be readily removed by grasping of tab 22 and manually tearing away of the tape. Stored within the internal chamber 18 is an elongated swab 24. The swab 24 includes a soft absorbent tip 26 which is usually of cotton. The tip 26 is sterilized by being wet with an isopropyl alcohol solution.

The closed end of the member 12 has attached thereto a pair of compartments 28 and 30. The outer end of the compartment 30 is permanently closed by a seal 32. The seal 32 will normally by reated by some form of heat sealing.

Separating the compartments 28 and 30 is a frangible seal 34. The frangible seal 34 will also be constructed by a heat seal but it is only sealed sufficiently so, if a manual compressive force is applied against the longitudinal length of the seal 34 as shown within FIG. 3, that the seal 34 will break. If there is a substance located within the compartment 28 and a second substance located within the compartment 30, upon breaking of the seal 34, these substances will intermix. In normal practice the substance to be contained within compartment 28 will be a sensitizer power which will usually comprise a magnesium compound. Located within the compartment 30 is to be a small quantity of water. The water and the magnesium are to be intermixed together on the breaking of the seal 34.

It has been presumed that the sealing means 20 has been broken and that the swab 24 has been removed with the tip 26 having come into contact with an area of a person which as believed to have been come into contact with marijuana. The swab 24 is then placed back into the first member tip 26 located adjacent the frangible seal 36. The substances located within the compartments 28 and 30 have now been intermixed and then frangible seal 36 is broken in a manner similar to the breaking of the frangible seal 34. This causes the intermixed substances to come into contact with the tip 26.

The operator then removes the swab 24 and places such within the second member 14 as shown within FIG. 5 of the drawing. The closed end of the member 14 includes a third compartment 38 which is permanently sealed at its outermost end by a permanent seal 40. The operator then effects breaking of the frangible seal 42 which then causes the substance located within the compartment 38 to come into contact with the tip 26 of the swab. The type of substance which will be normally contained within the compartment 38 will comprise a liquid solution of sodium hydroxide.

If the swab tip 26 was originally placed in contact with marijuana and has therefore received some cannabis, upon the tip 26 then coming into contact with the sodium hydroxide solution within the compartment 38, the tip 26 of the swab will change colors indicating the presence of cannabis. The color normally comprises a burnt orange or a rust brown.

Once the device 10 of this invention has been used, it is to be discarded and never to be reused.

What is claimed is:

1. A drug detection device comprising:

a housing having an internal elongated chamber constructed of a first member and a second member, said first member being attachable to said second member by a sealing means forming said internal chamber, said sealing means being removable permitting separation of said first and second members;

a swab located within said internal chamber with said first member being attached to said second member;

a first compartment attached to said first member at its closed end, a first frangible seal connecting said internal chamber and said first compartment, said first compartment being adapted to contain a quantity of a first substance;

a second compartment attached to said first compartment, a second frangible seal connecting said first compartment and said second compartment, said second compartment being adapted to contain a quantity of a second substance;

a third compartment attached to said second member at its closed end, a third frangible seal connecting said internal chamber and said third compartment, said third compartment being adapted to contain a quantity of a third substance; and whereby said sealing means can be broken permitting removal of said swab and after use of such is to be replaced within said internal chamber of said first member, said second frangible seal is to be broken causing mixing of said first and second substance, said first frangible seal is then to be broken causing contact of the intermixed substance of the intermixed first and second substances with the tip of said swab, said swab is to be removed from said first member and located within said second member, said third frangible seal is then to be broken causing contact of the tip of said swab by said third substance, upon a certain drug being present on the tip of said swab the tip will change color.

2. The drug detection device as defined in claim 1 wherein:

said housing being substantially cylindrical.

3. The drug detection device as defined in claim 2 wherein:

said first and second members being telescopingly interconnected together when such are interconnected together.

4. The drug detection device as defined in claim 3 wherein:

said housing being constructed of a transparent material.

* * * * *